(12) United States Patent
Lecuyer

(10) Patent No.: US 6,261,269 B1
(45) Date of Patent: Jul. 17, 2001

(54) DEVICES FOR DRAINING BIOLOGICAL FLUIDS

(75) Inventor: Alain Lecuyer, Grasse (FR)

(73) Assignee: NMT Neurosciences Implants S.A., Sophia Antipolis (FR)

( * ) Notice: Subject to any disclaimer, the term of this patent is extended or adjusted under 35 U.S.C. 154(b) by 0 days.

(21) Appl. No.: 09/350,288

(22) Filed: Jul. 9, 1999

(30) Foreign Application Priority Data

Jul. 10, 1998 (FR) .................................................. 98 08870

(51) Int. Cl.⁷ .................................................. A61M 5/00
(52) U.S. Cl. .................................. 604/250; 251/4; 251/10
(58) Field of Search .............................. 604/251, 93, 245, 604/256, 4.01, 167.01, 167.03, 264, 250, 153, 27, 34; 251/7, 4, 9, 10, 6

(56) References Cited

U.S. PATENT DOCUMENTS

| | | | |
|---|---|---|---|
| 3,826,256 | * | 7/1974 | Smith .................................... 604/159 |
| 5,011,468 | * | 4/1991 | Lundquist et al. ...................... 600/18 |
| 5,083,741 | * | 1/1992 | Sancoff ..................................... 251/9 |
| 5,116,324 | * | 5/1992 | Brierley et al. ....................... 604/180 |
| 5,346,470 | * | 9/1994 | Hobbs et al. ........................... 604/24 |
| 5,628,731 | | 5/1997 | Dodge et al. . |
| 5,730,731 | * | 3/1998 | Mollenauer et al. ................. 604/246 |
| 6,007,516 | * | 12/1999 | Burbank et al. ........................ 604/93 |

* cited by examiner

Primary Examiner—Richard K. Seidel
Assistant Examiner—Kevin C. Sirmons
(74) Attorney, Agent, or Firm—Dennison, Scheiner, Schultz & Wakeman

(57) ABSTRACT

The invention relates to devices for draining biological fluids. A first device comprises a housing (2) and a pinch valve (3) mounted in the housing, away from the walls of the latter. The housing includes an opening (11) arranged opposite the pinching means (6) of the valve. Another device (13) comprises a catheter section (7) of a drainage line and a member (12) for supporting the catheter, the catheter section passing into and emerging from the support member (12) at two points and forming a loop between these two points.

8 Claims, 2 Drawing Sheets

DEVICES FOR DRAINING BIOLOGICAL FLUIDS

FIELD OF THE BACKGROUND

The present invention relates to devices for draining biological fluids.

BACKGROUND OF THE INVENTION

Devices of this type are well known in the prior art. More particularly, French Patent Application No. 9716020 describes an external ventricular draining device comprising a catheter, one end of which is placed in the zone to be drained and the other end of which is connected to a drainage bag.

This device additionally comprises a pressure sensor placed on the catheter near its end situated towards the patient's head and an external pinch valve on this catheter. An electronically controlled power supply is provided in order to open the valve when the pressure exceeds a predetermined threshold. The pinch valve is of course re-usable, whereas the catheter is replaced after each use.

One problem encountered with this type of device is the difficulty in positioning the catheter in the pinch valve. Indeed, this positioning has to be done with very great care if the device is to function properly.

Furthermore, the catheter used must be compatible with the valve. In particular, its diameter and the flexibility of the material from which it is made must be appropriate. An error in the choice of catheter used can lead to malfunction of the device.

Finally, pinch valves, while being robust devices, nevertheless require certain precautions to be taken during their use and their storage. Thus, it is preferable for these valves, and in particular their pinching zone, to be protected by a housing.

SUMMARY OF THE INVENTION

The present invention aims to overcome these drawbacks.

More particularly, the invention aims to provide devices which can be used for draining biological fluids with the aid of a catheter and means for pinching this catheter to ensure that the latter is perfectly adapted to the pinching means. The invention also aims to provide means permitting suitable engagement of the catheter in these pinching means. The invention further aims to provide means for draining biological fluid whose pinching means are protected.

To this end, the subject of the invention in the first instance is a device for draining biological fluids, characterized in that it comprises a housing with walls and a pinch valve comprising pinching means, the said valve being mounted in the housing, away from the said walls, the said housing including an opening arranged opposite the pinching means, means also being provided to engage a catheter section of a drainage line in the said pinching means via the said opening.

The subject of the invention is also a device for draining biological fluids, characterized in that it comprises a catheter section of a drainage line and a member for supporting the catheter, the said catheter section passing into and emerging from the said support member at two points and forming a loop between the said two points, the said support for the catheter having a cut-away leaving a part of the said loop free in order to allow it to be pinched by pinching means.

It will be appreciated that the two devices which have just been described are designed to cooperate, even though they are not physically joined until the time of use. In particular, the catheter support is of such a shape that it can be introduced into the opening in the housing in such a way as to bring that part of the catheter left free by the cut away into the pinching means of the valve mounted inside this housing.

The invention makes it possible to overcome the drawbacks which were mentioned above. This is because, in the first instance, the catheter support can be guided upon its entry into the housing by any suitable means in such a way that the free part of the loop of the tube engages perfectly in the pinching means of the valve.

Furthermore, with the valve being placed in the housing away from the walls of the latter, the catheter section of the drainage line must necessarily be brought into the pinching means via the opening in the housing. Thus, by giving this opening suitable dimensions, it is possible to ensure that the catheter cannot be actually put into position manually.

In these circumstances it is also certain that a catheter having the appropriate characteristics will be used. It suffices to make the catheter section used and its support and introduction member inseparable.

Finally, the pinch valve and in particular its pinching means are protected by the housing.

In one particular embodiment of the invention, the said catheter support comprises elastic means for immobilizing it in relation to the said pinching means.

These elastic means can in particular cooperate with that wall of the housing in which its opening is formed.

Again in one particular embodiment, the said catheter support forms a flat cassette designed to be introduced into a slot in the said pinching means.

In this case, the aforementioned opening formed in the housing is therefore in the shape of a slot, which shape corresponds to the cross section of the cassette.

More particularly, the said cassette can be T-shaped, the said catheter passing into and emerging from the cassette at the ends of the horizontal bar of the T, and the said loop being formed in the vertical branch of the T.

In this case, the devices can be designed in such a way that, during their use, only the horizontal bar of the T of the cassette protrudes from the slot in the housing, this bar thereby forming a grip element for removing the cassette from the slot.

It is also possible to provide that the said loop forms a catheter part separate from an inlet part and from an outlet part, which is joined in the said catheter support to the said inlet and outlet parts.

It is thus possible for the loop of the catheter to be made of a material particularly suited to its use in a pinch valve, the rest of the catheter having different characteristics.

BRIEF DESCRIPTION OF THE DRAWINGS

One particular embodiment of the invention will now be described by way of non-limiting example and with reference to the appended diagrammatic drawings, in which.

DETAILED DESCRIPTION OF A PREFERRED EMBODIMENT

Figure 1A:
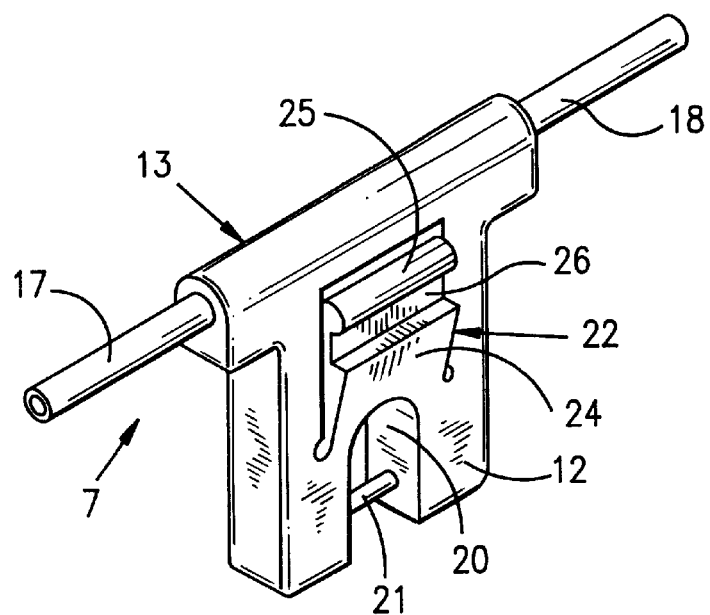
FIG. 1a is a perspective view of one of the devices forming the subject of the invention.
Figure 1B:
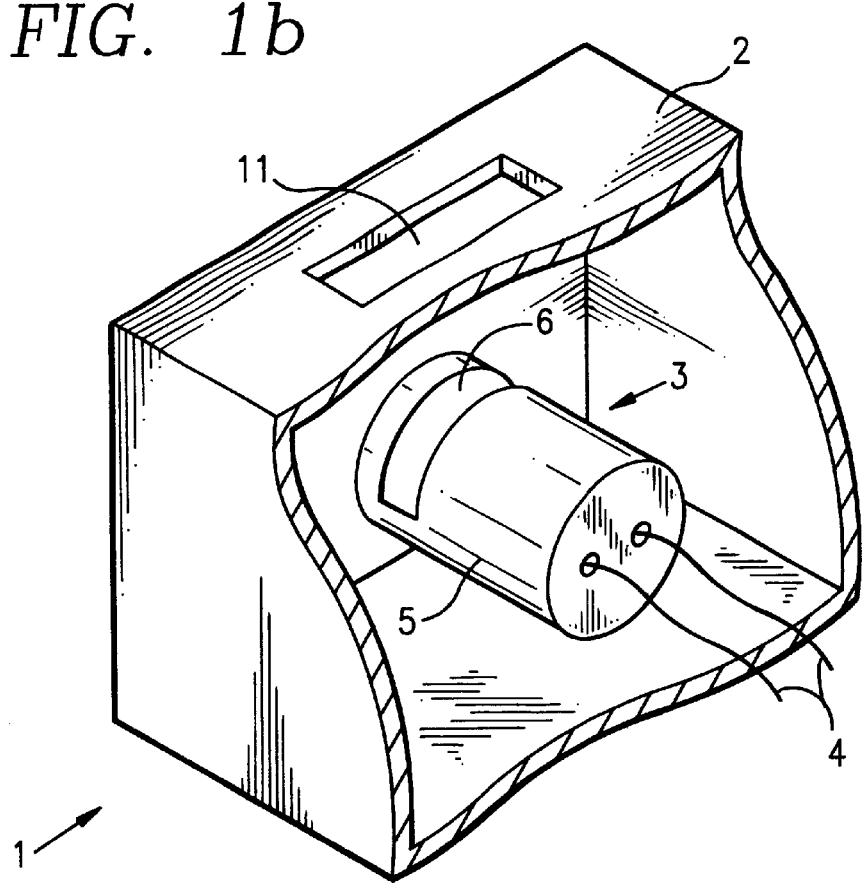
FIG. 1b is again a perspective view, partially cut away, of the other device of the invention.

FIG. 1b shows a device 1 for draining biological fluid, including essentially a housing 2 in which a solenoid pinch valve 3 is mounted in any suitable manner away from the walls of the housing 2. Electrical supply wires 4 for the solenoid valve 3 emerge from the housing 2.

Figure 2:
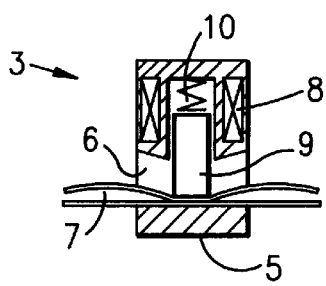
FIG. 2 is a diagrammatic cross section of a pinch valve that can be used in the invention.
Figure 5:
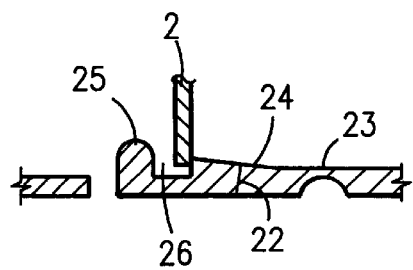
FIG. 5 is a cross section through part of this device.

The solenoid valve 3 is represented in more detail in FIG. 2.

This solenoid valve is made up of a body 5 forming a bracket which creates a slot 6 in which a catheter 7 can be engaged so as to be closed by being pinched.

One of the branches of the body 5 receives an electromagnet whose coil 8 is supplied via the wires 4. The core 9 of this electromagnet forms a plunger which is able to pinch the catheter 7 against the other branch of the body 5. A compression spring 10 is placed between the body and the core 9 so as to push the core in the direction of the catheter 7 and pinch the latter.

Returning to FIG. 2, it will be seen that the upper wall of the housing 2 has an opening 11 in the form of a slot located directly opposite the slot 6 in the solenoid pinch valve 3.

As is shown in FIG. 1a, the catheter 7 is here integral with a cassette 12 forming, with the catheter 7, the other device 13 forming the subject of the invention.

The cassette 12 is made of moulded plastic, starting from two half-cassettes 14 and 15 which are joined together to form a space accommodating the catheter and are bonded with the aid of bonding pins 16.

Figure 3:
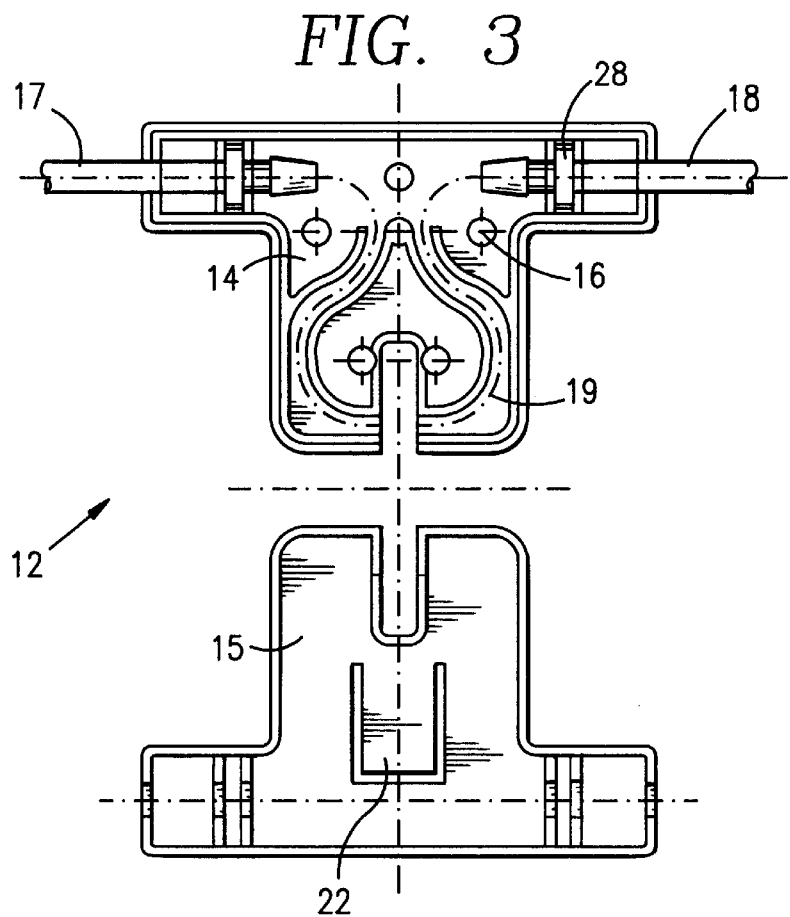
FIG. 3 is a plan view of one of the devices forming the subject of the invention, before its assembly.
Figure 4:
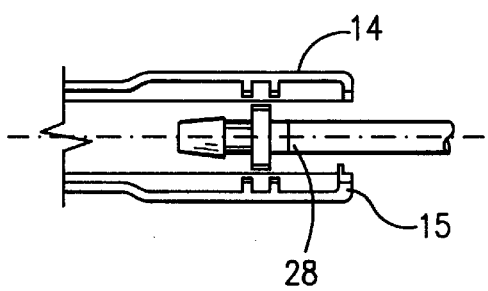
FIG. 4 is a plan view of this device, in the course of assembly.

The cassette 12 has the general shape of a T. An inlet part 17 of the catheter passes into the cassette 12 at one end of the horizontal bar of the T, and an outlet part 18 of the catheter emerges from the cassette 12 at the other end of this bar. Between these inlet and outlet parts of the catheter, a loop part, represented in FIG. 3 merely by its axis 19, is accommodated inside the vertical bar of the T. Connections 28 serve to connect the various parts 17, 19 and 18 of the catheter 7.

The vertical branch of the T forming the cassette 12 has a cross section of the same shape as the slot 11, so that it can be slid into this slot. Moreover, this branch includes a cut-away 20 which leaves a part 21 of the loop of the catheter free.

When the cassette 12 is engaged in the slot 11 with the horizontal bar of the T protruding from this slot, the free part 21 of the catheter is engaged in the slot 6 between the housing 5 and the core 9.

Finally, the part 15 of the cassette 12 includes an elastic tongue 22 to which it is connected via a bridge of material 23 forming a hinge. The tongue 22 has an inclined surface 24 separated from a part forming a pusher 25 by a notch 26.

When the cassette 12 is engaged in the slot 11, the edge of the latter cooperates with the ramp 24 in order to bend the tongue 22 towards the inside of the cassette. When the cassette 12 reaches the end of its travel, the wall of the housing 2 snaps into the notch 26 and thereby locks the cassette 12, rendering it integral with the housing 2.

It is only by pressing on the pusher 25 and gripping that part of the cassette 12 protruding from the slot 11 that it is possible to unlock this cassette and remove it from the housing. Any inadvertent removal is thereby rendered impossible.

What is claimed is:

1. Device (13) for draining biological fluid characterized in that is comprises a catheter section (7) of a drainage line and a member (12) for supporting the catheter, said catheter section (7) passing into and emerging from the support member (12) at two points and forming a loop (19) between the two points, said member for supporting the catheter having a cut-away (21) leaving a part (22) of said loop free in order to allow it to be pinched by pinching means wherein said member (12) for supporting the catheter forms a flat cassette, designed to be introduced into a slot (11) in the said pinching means.

2. Device according to claim 1, in which the said cassette is T-shaped, the said catheter passing into and emerging from the cassette at the ends of the horizontal bar of the T, and forming the said loop in the vertical branch of the T.

3. Device according to claim 2, in which the said loop forms a catheter part separate from an inlet part (17) and from an outlet part (18), which is joined in the said catheter support to the said inlet and outlet parts.

4. Device according to claim 2, in which the said loop forms a catheter part separate from an inlet part (17) and from an outlet part (18), which is joined in the said catheter support to the said inlet and outlet parts.

5. Device according to claim 1 wherein said cassette is formed from first and second elements joined together to define a space for receiving the catheter.

6. Device according to claim 1 wherein said support member (12) is T shaped and wherein said cut-away is formed in a vertical branch of the T.

7. Device (13) for draining biological fluid characterized in that is comprises a catheter section (7) of a drainage line and a member (12) for supporting the catheter, said catheter section (7) passing into and emerging from the support member (12) at two points and forming a loop (19) between the two points, said member for supporting the catheter having a cut-away (21) leaving a part (22) of said loop free in order to allow it to be pinched by pinching means, said member (12) for supporting the catheter comprising elastic means (23) for immobilizing the catheter in relation to the pinching means and forming a flat cassette, designed to be introduced into a slot (11) in the said pinching means.

8. Device (13) for draining biological fluid characterized in that is comprises a catheter section (7) of a drainage line and a member (12) for supporting the catheter, said catheter section (7) passing into and emerging from the support member (12) at two points and forming a loop (19) between the two points, said member for supporting the catheter having a cut-away (21) leaving a part (22) of said loop free in order to allow it to be pinched by pinching means, wherein said member (12) for supporting the catheter comprises elastic means (23) for immobilizing the catheter in relation to said pinching means and said loop forms a catheter part separate from an inlet part (17) and from an outlet part (18), which is joined in the said catheter support to the said inlet and outlet parts.

* * * * *